(12) United States Patent
Neuss

(10) Patent No.: US 10,881,386 B2
(45) Date of Patent: Jan. 5, 2021

(54) DEVICE FOR CLOSING DEFECTS IN THE VASCULAR SYSTEM

(76) Inventor: Malte Neuss, Bonn (DE)

(*) Notice: Subject to any disclaimer, the term of this patent is extended or adjusted under 35 U.S.C. 154(b) by 576 days.

(21) Appl. No.: 12/934,878

(22) PCT Filed: Mar. 26, 2009

(86) PCT No.: PCT/EP2009/002225
§ 371 (c)(1),
(2), (4) Date: Nov. 16, 2010

(87) PCT Pub. No.: WO2009/118182
PCT Pub. Date: Oct. 1, 2009

(65) Prior Publication Data
US 2011/0054519 A1    Mar. 3, 2011

(30) Foreign Application Priority Data
Mar. 26, 2008  (DE) .................. 10 2008 015 781

(51) Int. Cl.
*A61B 17/00*   (2006.01)
*A61F 2/01*    (2006.01)
(Continued)

(52) U.S. Cl.
CPC .... *A61B 17/0057* (2013.01); *A61B 17/12022* (2013.01); *A61B 17/12109* (2013.01); *A61B 17/12113* (2013.01); *A61B 17/12122* (2013.01); *A61B 17/12172* (2013.01); *A61B 17/12177* (2013.01); *A61F 2/01* (2013.01); *A61F 2/91* (2013.01); *A61B 2017/00243* (2013.01); *A61B 2017/00575* (2013.01); *A61B 2017/00597* (2013.01); *A61B 2017/00606* (2013.01); *A61B 2017/00623* (2013.01); *A61B 2017/00867* (2013.01); *A61B 2017/12054* (2013.01); *A61B 2017/12095* (2013.01); *A61F 2/011* (2020.05); *A61F 2/2418* (2013.01); *A61F 2/2427* (2013.01); *A61F 2/2475* (2013.01); *A61F 2002/016* (2013.01); *A61F 2002/018* (2013.01); *A61F 2002/068* (2013.01); *A61F 2220/0075* (2013.01); *A61F 2230/005* (2013.01);
(Continued)

(58) Field of Classification Search
CPC .......... A61B 17/0057; A61B 17/12172; A61B 17/12177; A61B 17/12113; A61B 17/12122; A61B 2017/00575; A61B 2017/00597; A61B 2017/00606; A61F 2002/016; A61F 2002/018
USPC ........................ 606/151, 157, 158, 200, 213
See application file for complete search history.

(56) References Cited

U.S. PATENT DOCUMENTS 5,683,411 A * 11/1997 Kavteladze et al. .......... 606/200
5,853,422 A * 12/1998 Huebsch ............ A61B 17/0057
606/157
(Continued)

*Primary Examiner* — Alexander J Orkin
(74) *Attorney, Agent, or Firm* — Brooks Kushman P.C.

(57) ABSTRACT

The invention relates to a self-expanding device, particularly an implant, for closing defect openings in the human or animal body, which device, in a first state, has the shape of an elongated tube (2) with slotted segments and, in a second state, has a shortened shape with formation of at least one open or substantially closed hollow structure (3) of considerable transverse extent, where in the slotted segments of the tube (2) form individual webs (16) that are each connected to adjacent webs (16), such that a net-like overall structure is obtained in the second state.

12 Claims, 11 Drawing Sheets

(51) Int. Cl.
*A61F 2/91* (2013.01)
*A61B 17/12* (2006.01)
*A61F 2/24* (2006.01)
*A61F 2/06* (2013.01)

(52) U.S. Cl.
CPC .......... *A61F 2230/0006* (2013.01); *A61F 2230/0067* (2013.01); *A61F 2230/0078* (2013.01); *A61F 2230/0093* (2013.01)

(56) References Cited

U.S. PATENT DOCUMENTS

| | | | | |
|---|---|---|---|---|
| 5,928,260 | A * | 7/1999 | Chin | A61B 17/12022 604/107 |
| 5,944,738 | A * | 8/1999 | Amplatz et al. | 606/213 |
| 6,063,113 | A * | 5/2000 | Kavteladze | A61B 17/0057 606/200 |
| 6,241,746 | B1 * | 6/2001 | Bosma et al. | 606/200 |
| 6,440,152 | B1 * | 8/2002 | Gainor et al. | 606/213 |
| 2002/0082627 | A1 * | 6/2002 | Berg | A61B 17/0057 606/155 |
| 2002/0156499 | A1 * | 10/2002 | Konya et al. | 606/213 |
| 2003/0171774 | A1 * | 9/2003 | Freudenthal et al. | 606/213 |
| 2004/0073155 | A1 * | 4/2004 | Laufer | A61B 8/12 604/8 |
| 2004/0073242 | A1 * | 4/2004 | Chanduszko | A61B 17/0057 606/157 |
| 2005/0043759 | A1 * | 2/2005 | Chanduszko | 606/213 |
| 2005/0049681 | A1 * | 3/2005 | Greenhalgh et al. | 623/1.15 |
| 2005/0288705 | A1 * | 12/2005 | Gilson et al. | 606/200 |
| 2006/0217760 | A1 * | 9/2006 | Widomski | A61B 17/0057 606/213 |
| 2006/0224183 | A1 * | 10/2006 | Freudenthal | 606/213 |
| 2007/0066993 | A1 * | 3/2007 | Kreidler | A61B 17/0057 606/213 |
| 2007/0129755 | A1 * | 6/2007 | Abbott et al. | 606/213 |
| 2008/0200945 | A1 * | 8/2008 | Amplatz et al. | 606/195 |
| 2008/0249562 | A1 * | 10/2008 | Cahill | 606/215 |
| 2009/0088795 | A1 * | 4/2009 | Cahill | 606/215 |

\* cited by examiner

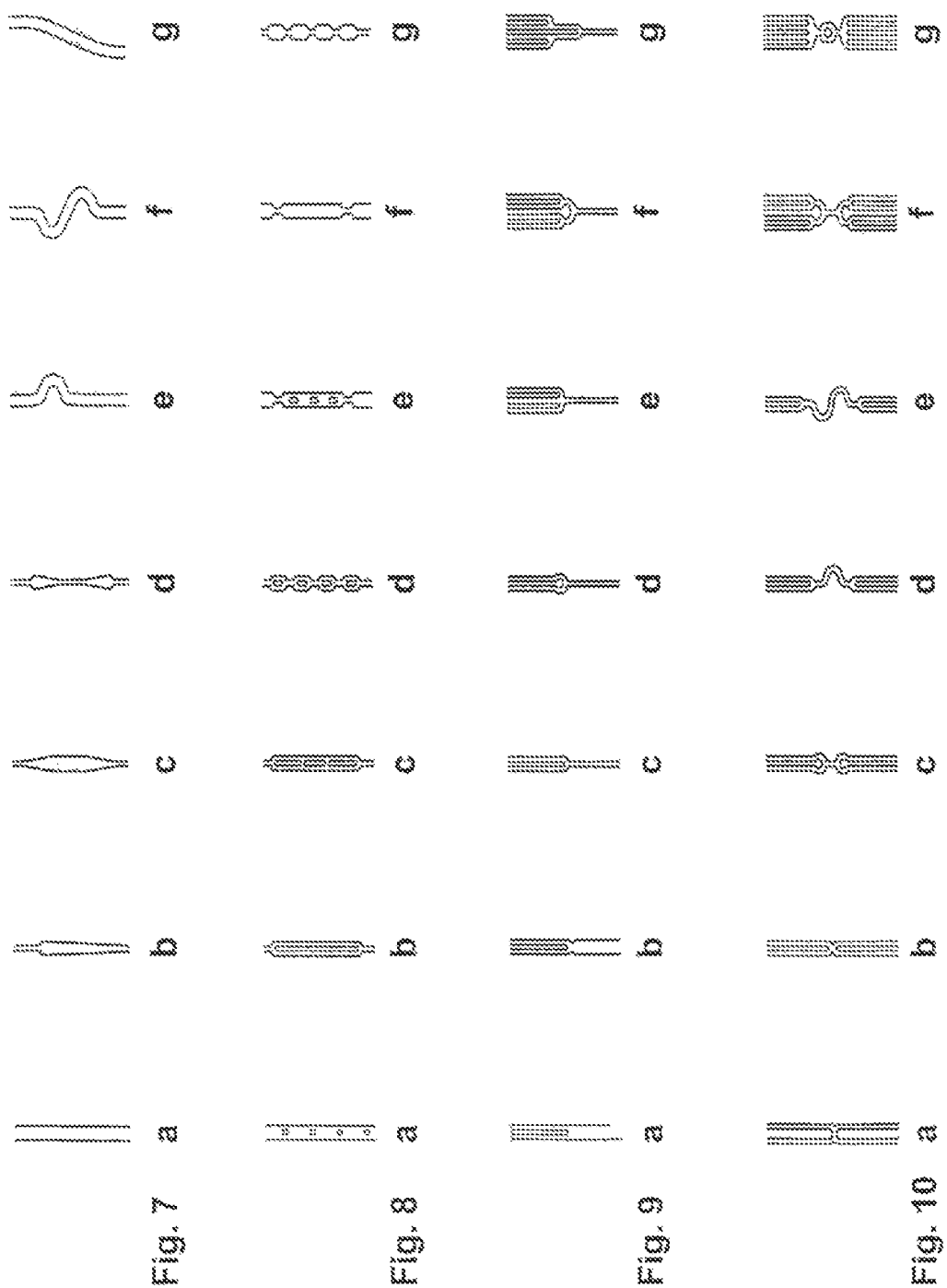

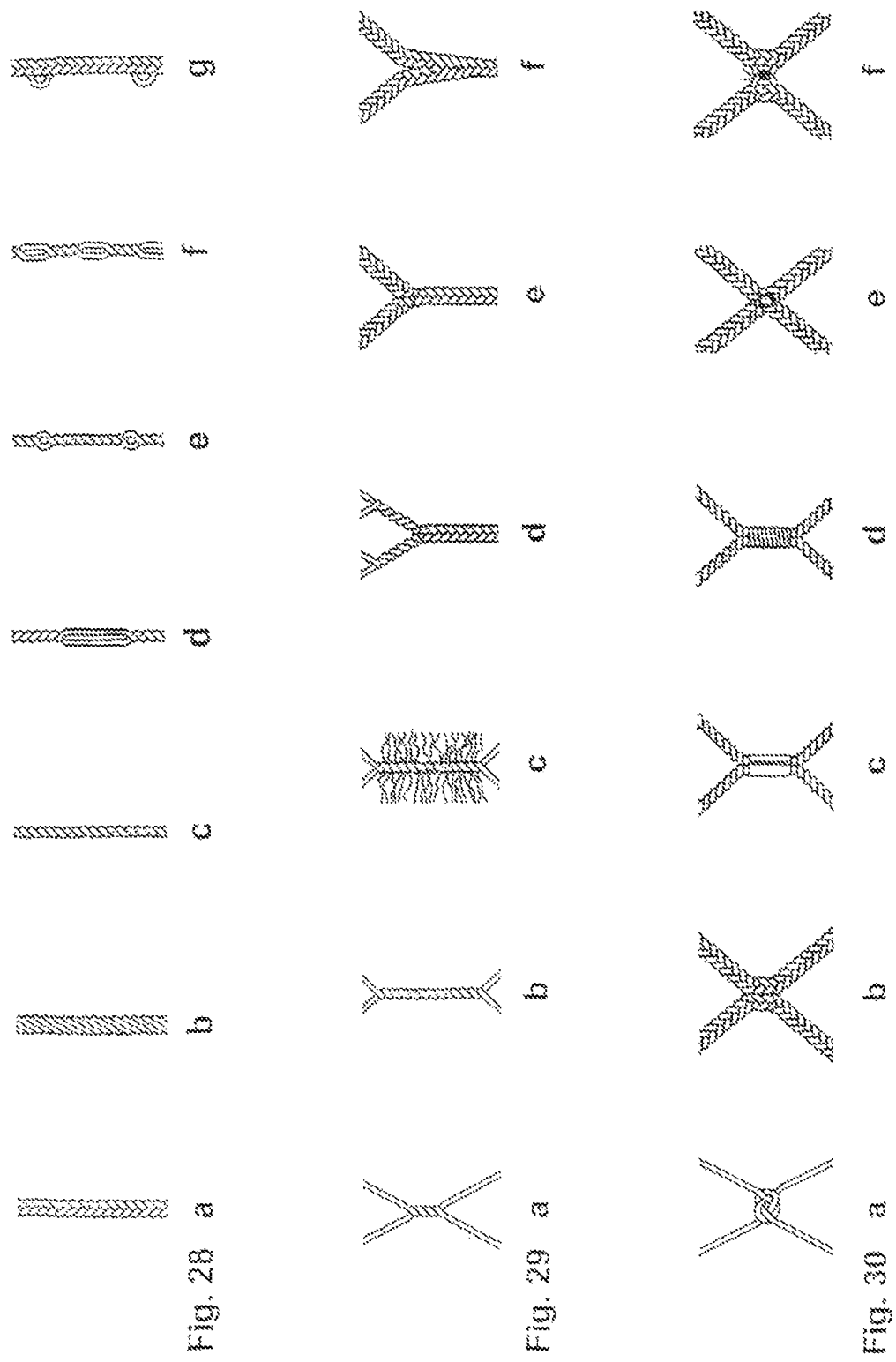

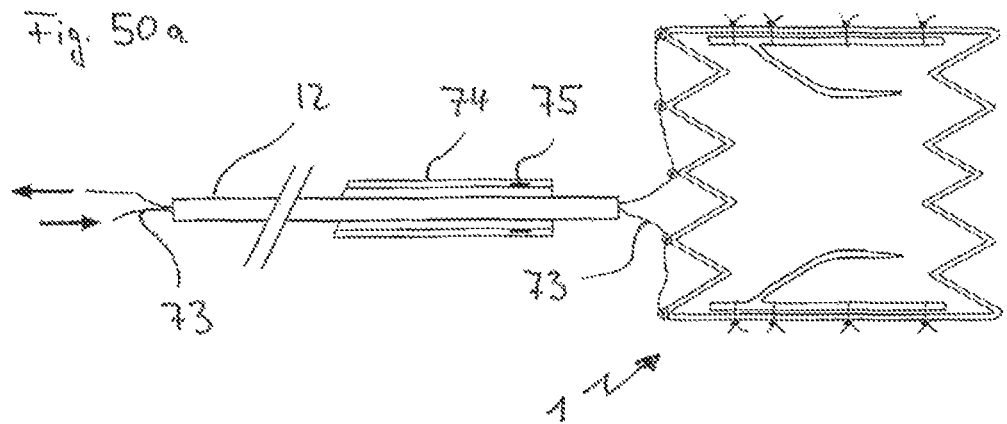
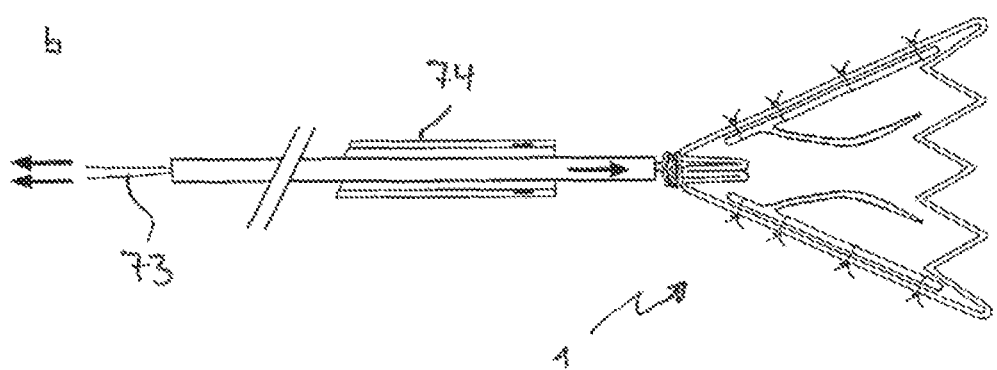
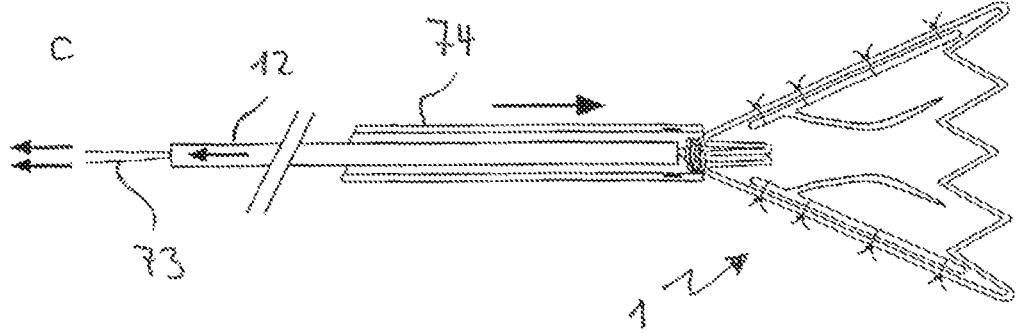

DEVICE FOR CLOSING DEFECTS IN THE VASCULAR SYSTEM

The present invention is with regard to a device for intervention therapy for vascular malformations such as, for example, to seal septal defects in human or animal bodies. It can be used by means of catheter technology in the case of therapy for heart failure with a left-to-right shunt e.g., of an atrial septal defect (ASD) or of a patent foramen ovate (PFO).

Efforts are being made since a long time to use catheter technology to close vessels that are surgically difficult. Catheter intervention is less burdensome for the patient than an operation and simple sedation is, possibly, sufficient.

Septal defects of the heart have also been closed since a long time by means of catheter technology. The first transcatheter closures of atrial septal defects were conducted in 1976 by King and Mills (Mills N. K., King T. D.; Nonoperative Closure of Left-to-right Shunts; J. Thorac. Cardiovasc. Surg. 72: 371-378, 1976) in animal experiments and in humans. The closing device used and another umbrella system that was developed by Rashkind (Rashkind W. J., Mullins C. E., Hellenbrand W. E., et al; Nonsurgical Closure of Patent Ductus Arteriosus: Clinical Application of the Rashkind PDA Occluder System; Circulation 75: 583-592, 1987), never had a broad clinical application due to the size of the insertion sheath of initially, 23 F in the case of the first device mentioned and the fastening hooks in the case of the insertion device by Rashkind and the double umbrella by Rashkind.

A further development of this umbrella system presents the hexagonal umbrella under the name Intrasept manufactured by the company Cardia (www.cardia.com) for PFO closure. The differently angulated progression of PFO has to allow for a double hinge joint between the two umbrellas. The disadvantage in the case of closure of larger defects is the absence of self-centring.

Two other closure devices are the so-called "Clamshell Device" by Lock (Lock J. E., Rome J. J., Davis R. et al; Transcatheter Closure of Atrial Septal Defects, Experimental Studies, Circulation 79: 1091-1989) and the "Buttoned Device" by Sideris (Sideris E. B., Sideris S. E., Fowlkes J. P. et al; Transvenous Atrial Septal Defect Occlusion in Piglets with a "Buttoned" Double-disk Device; Circulation 81: 312-318, 1990) that essentially exhibit an umbrella-type shape with metal bars extended from the centre without or with spring hinges as carriers of a fabric covering. Problems with regard to the "Clamshell Device" comprise spontaneous embolisation of the device, remaining residual shunts and wire breakage. The disadvantages of the "Buttoned Device" are an inconvenient implantation technique, remaining residual defects and embolisations.

D. Pavcnik et al. describe an insertion device made from stainless pinnate metal spiral beads that is covered by two layers of nylon mesh in Cardiovasac Intervent Radiol (1993) 16: 308-312. Three pieces of a spiral coil are stitched onto the rear of the disc and function as an anchor. The self-expanding disc opens in the left atrium upon exiting the insertion sheath. Anchoring wires on the rear anchor the umbrella at the septal wall. The disadvantage in the case of this insertion device is that the disc moves laterally away from the implantation catheter and has first to be intricately turned by 90 degrees in the left atrium.

Another device with which to close atrial septal defects of the heart is described in Circulation volume 88, No. 4, Part 1, October 1993. The device consists of two quadratic frames made from super-elastic nitinol wire. One quadratic frame of stretching wire is formed at the corner of the frame as well as at the midpoints of the sides of the flexible loops. The eight loops in each frame facilitate folding up of the frame in order to insert the same into the implantation catheter. Both wire frames are respectively covered with one Dacron fabric (polyester) that are stitched to one another and, thus, form two connected panels. The disadvantage in the case of this double umbrella was that it required a catheter diameter of at least 12 F and was difficult to reposition. The system was removed from the market due to damages to the surrounding vascular structures caused by the stiff wire frame at the corners.

Another self-expanding device with which to close defect openings or vessels and which also consisted of interlocking or partially braided wire bundles was established in WO 95/27448. The disadvantage with this umbrella system is that it cannot be re-positioned and that the insertion catheter's diameter has, mandatorily, to be increased due to the interlocking wire filaments.

A device with which to close defect openings or vessels and that consists of interlocking wire bundles that are welded together at both ends respectively is established in U.S. Pat. No. 5,108,420. When folded up in an insertion catheter, the device takes on an elongated form and takes on a second umbrella-like shape after exiting the insertion catheter due to the material's re-set forces. A sewed-in membrane made from polyester (Dacron) should accelerate defect closure. This umbrella system can be re-positioned due to a screw joint welded at one side.

The device is held in position due to a clamping effect. This umbrella system has several disadvantages. Often, the umbrella does not position itself optimally adjacent to the septal wall and, in doing so, hampers blood flow in the heart. It cannot be placed above a recumbent guidewire, thereby considerably hampering positioning in the case of an insertion catheter that is not recumbent at right angles to the defect. The umbrella system can be pushed in the radial direction with regard to the opening after implantation has taken place. Blood can adhere to the screw joint so that disconnection is not possible or the same can be displaced by the reaction torque when unscrewing the umbrella. In addition, the umbrella often does not reconfigure itself flat to the defect wall which could result in impeding blood flow. As a VSD closing umbrella, it can cause severe cardiac arrhythmias because it is too stiff.

The same also applies to the umbrella system described in patent specification DE 10 2005 053 958 in which the wires are welded together only at one side.

An umbrella-like device that also comprises wires that are welded together is established in DE 196 04 817. The disadvantage here is that the umbrella's covering material cannot be securely stitched to the wires and can, therefore, slip.

Another umbrella system that is fashioned from a tube with a longitudinal slit is established in DE 100 00 137. Loops are affixed to the individual strips in order to reliably fasten threads for the umbrella covering material. The disadvantage here is the high rigidity of this umbrella system and a complicated release mechanism.

A further umbrella system by the name Helex has been established by the company, L. Gore. This comprises a G-shaped frame made from nitinol wire that is covered with a PTFE membrane. The disadvantage here is that, in the case of incorrect positioning, this cumbersome umbrella system can only be re-positioned in a restricted manner, occasionally resulting in wire breakage of the umbrella frame. Interventional recovery after detachment is difficult.

Another umbrella system by the name Solysafe by the company Swissimplant (www.solysafe.com) cannot be aligned to the varying lengths of the PFO (patent foramen ovale). Umbrellas stretched in the metal baskets are implanted by a wire splint and held together by a click connection. The disadvantage here is the wire basket diameter which is large in comparison to the umbrella's diameter.

An additional umbrella system called Premere by the company, Velocimed (www.velocimed.com) can be aligned to the varying lengths of the PFO (patent foramen ovale) with sutures. The clover-leaf shaped umbrellas are respectively made from a nitinol sheet. This umbrella system is, to date, not suitable for a normal septal defect closure.

An umbrella comprising a wire basket in which the two sub umbrellas can be screwed to one another at the defect wall after positioning is established by the company Carac (www.carag.com). The disadvantage here is that removal of the umbrella after screwing it in place can only take place surgically.

The closure plug for the left cardiac atrium is distributed under the name PLAATO Device by the company ev3. In this case, the same deals with a self-expandable spherical wire cage with hooks that is provided with a PTFE foil. This closure system is only suitable as a plug for the closure of antra and large vessels but not for defect closure.

The objective of the present invention is to provide a device with which to close defect openings in human or animal bodies, which does not exhibit the disadvantages of the devices mentioned above.

The objective is met by a self-expanding device, particularly an implant for closure of defect openings in human or animal bodies, which, in the first state, has the shape of an elongated tube with slit segments and, in the second state, takes on a shortened shape during re-formation of at least one open or (essentially) closed hollow structure with large lateral expansion, whereby the slit segments of the tube form individual strips that are respectively connected to the adjacent strip so that an overall net-like structure emerges when in the second state.

The self-expanding device is, in particular, a vascular implant, which, in the first state, resembles the elongated shape with the slit segments of a conventional vascular stent. In the second state, that is adopted, for example, after cessation of an outer force through a sheath or in a catheter, this elongated and slit tube expands with substantial shortening in the middle piece to an at least hollow structure, for example, in the shape of a ball, a bell, one or several umbrellas, as is required, in order to, for example, fill the vascular defect or to close the same. During this transformation, the proximal and distal ends of the device essentially retain their tubular character i.e., they do not participate in the transformation or do so only to a minimal extent.

For the purpose of the invention, "distal" indicates that part of the device that faces the treating doctor or the catheter, while "proximal" refers to that part that faces the body and does not face the treating doctor.

The device, in accordance with the invention, adopts a markedly shortened shape in the expanded second state during radial expansion. As a rule, this expansion is so great that the diameter of the device exceeds its length in the second state. The extent of the expansion, however, depends upon the circumstances and upon the type and size of the defect to be treated.

The hollow structure can, basically, take on any shape such as, for example, a spherical shape, an umbrella shape, a bell shape, the shape of an ellipsoid, a disc, a bell, depending upon the requirement of the application. There could also be several hollow structures such as, for example, two umbrella-like, rosette-shaped structures with a short length and large lateral expansion.

When using a laser from a pre-cut device in accordance with the invention, it is advantageous to cut diagonally running strips from the tube at the points with great direction change/tension in order to minimise flexural stress during transformation and during installation of the hollow structures. This applies, in particular, to the peripheral parts of the hollow structure especially umbrellas.

The same also applies to the middle piece between two umbrella-like, rosette-shaped structures. On the one hand, tension can also be minimised here by the strips running diagonally in the tube. On the other hand, this design, however, also permits a self-centring of the device in a defect and prevents slipping of the umbrella system within the defect. The diagonally parallel segments or sections in the middle piece between two double umbrellas should, however, be connected to one another section-wise in order to increase stability.

The exemplary embodiment with two umbrella-like, rosette-shaped structures of short length and large lateral expansion is especially suited for closure of an ASD or PFO by means of catheter technology. The invention will, first and foremost, be described below by means of this type of double umbrella structure. A neck comprising a shorter or longer stent-like structure that is aligned to the diameter and shape of the defect is located in the middle piece between these two umbrella-like structures.

These stent-like structures splint the defect and prevents lateral slipping in the defect. As a result of the material-related clamping force between the two umbrella-like structures, both are flexibly pressed from both sides to the remaining septal wall around the defect. This ensures that the device can be implanted simply and quickly and cannot be pushed any more within the opening after implantation. The device is, consequently, considerably more flexible for insertion and does not need to, any longer, be aligned so precisely to the size and geometry of the defect opening. This is of great significance especially for closure of intra-cardiac defects since these defects do not usually exhibit a circular cross-section but an oval one instead.

It is of advantage if the stent-like structures between the two umbrella-like structures support themselves elastically in this implanted state against the rim of the opening to be closed and, thereby, effect self-centring.

The device of the present invention can, in addition, contain fabric-like membranes that are respectively placed on the netted umbrella structure.

The device is, advantageously, produced by creating suitable multiple slits, by means of a laser cutting procedure, with three up to 200, preferably 6 to 72 slits on the circumference of a spring-elastic tube with a diameter of 0.2 to 5 mm, preferably 1 to 3 mm and with a wall thickness of 0.01 to 0.3 mm, preferably 0.05 to 0.15 mm, so that n number of (3 to 200) individual strips emerge on the circumference as a result of slitting. The individual strips should be at least be connected to one another in pairs, exhibit an approximately square or rectangular cross-sectional shape and have a length of 0.5 to 50 mm, preferably 1 to 10 mm, and exhibit an overall netted lattice structure after transformation in the second state. Depending on the outer shape, the outer umbrella parts can be designed to resemble a rosette after transformation in the second state. The induction tube does not, preferably, have slits at one or both ends respectively for a length of 0.3 to 3 mm in order to enable the umbrella-like second structure to easily fold up again for passage through an insertion catheter and for incorporation of a repositioning mechanism at the proximal side and formation of an umbrella button on the other distal side. The tube can only be rounded there and be hollow inside for better guidance of the umbrella system by a guidewire or be welded to a plug in order to avoid sharp edges. Individual strip lengths could each be of the same length, be located along the entire tube's length or each be slightly staggered parallel or diagonal to the longitudinal axis of the tube. The length of the strips could be in the longitudinal direction of the tube but also of varying lengths.

For all strip lengths of the tube in the first state, it applies that the product of the maximum strip length multiplied by the number n of strips should correspond at least 3.2 times to 9 times of the respective umbrella diameter, preferably 3.3 to 5 times.

Thus, the number of strips in the middle piece between the two umbrella parts as well as the strip lengths should be less than in the areas with a maximum umbrella diameter.

Broader strips or double strips can be provided if a greater rigidity is required in certain umbrella sections. Should less rigidity of the individual umbrella sections be required, as in the outer area of the individual umbrellas, the same can be achieved through removal of material by providing additional recesses, in situ grinding or intensified electropolishing. The individual strips can exhibit varying lengths along their progression, can be straight, can be slightly curved or can be S-shaped. They can, in addition, be furnished with grooves or loops in order to facilitate stitching of the umbrella material.

The force effect on the defect rim to relieve the surrounding fabric can be kept to a minimum due to the greater number of strips as well as a greater breadth of the strips. However, in contrast to the devices of prior art, defects can also be closed with adequate reliability using devices that are, compared to the ideal case, too large or too small due to self-centring of the device.

As in the case of vascular stents too with which to keep vessels open, connecting elements between the individual strips can have different shapes and can be X-shaped, H-shaped, C-shaped or curved.

The individual strips in the second, expanded state should preferably respectively collectively form approximately quadrangular parallelograms, rhombi or hexagons that are each connected at the tip to the next parallelogram or the next rhombus in order to facilitate retrieval of the umbrella system in the insertion catheter in the case of erroneous positioning, without the umbrella parts hooking into the insertion catheter. In the case of a polygon or a lattice-shaped structure made from curved strips, the total length of the individual strips on both sides between two connecting points should each be equal. Only then will they permit the individual lattice segments to fold together optimally.

The umbrella system in another preferred embodiment has an M-shaped contour in the second state. The stent area in the middle piece between the two umbrella structures can also be connected to elastic elements in order to better follow the pulsating wall thickness changes of a septal wall or in order to counterbalance varying umbrella angles without having one umbrella part project from the septal wall as is more often the case with other umbrella systems in closures of patent foramen ovate (PFO).

The stent area in the middle piece between two umbrella parts can also be composed of only spirally located strips that align themselves differently of their own accord to defect diameters so that a rotary motion takes place during the transition from the elongated state in the implantation catheter to the expanded state, in which the spirally located strips move outward in a radial direction from the longitudinal axis and, in doing so, support themselves elastically at the rim of the opening to be closed. The two umbrella parts can come close to one another till they make contact as a result of this rotary movement. Thereby, the centring support within the opening to be closed as well as a form fit of the device at both sides of the fabric covering the opening is achieved. It is particularly advantageous if the two outer umbrella structures are approximately equal in size, exhibit a round shape when viewed from above and, respectively, lie flat and close adjacent to the defect wall in the side view.

An alternative, transverse-oval umbrella shape of both sides when viewed from the top is an advantage, for example, when closing the perimembranous ventricular septal defect in cases where there is very little space between the defect and the valvular structure which the umbrella should not touch, under any circumstances, since there is the danger of a valvular perforation due to long-term stress. In the case of transverse-oval or quadrangular umbrellas, it is an advantage to have a radiopaque marker in a defined position at the rim of the umbrella, approximately at the lower rim, for orientation of the umbrella position during implantation.

The umbrella structure is preferably formed from a tube. The tube can be made from any spring-elastic, medically compatible material, can consist of surgical steel and cobalt-chrome alloy with elastic characteristics or an absorbable metal such as magnesium or ferrous alloys, for example, or comprise an absorbable synthetic material such as polylactide or polydioxanone with elastic characteristics. Nickel titanium alloys with shape memory such as nitinol are, however, preferred. The transformation and spring effect can, for example, be achieved and/or set by a specific thermal treatment. Synthetic materials with shape memory are specifically included.

Wires connected at the ends or, better still, flexible wires or braided wires that assume a tubular shape can be also used at least once instead of a tube. The cross-section of the wire can be round, oval, semicircular, quadratic or rectangular, for example, and can also vary along the length of the wire.

Alternatively, a synthetic material with corresponding elastic characteristics can also be used, which is offered especially in the case of elements that are formed from a primary tube. The wire-shaped elements could, if required, be wrapped with platinum or gold or tungsten wire or be provided with platinum or gold rings in order to increase X-ray contrast. If the umbrella elements are formed from flexible wires or braided wires that are merged, it is particularly advantageous to work individual platinum or gold wires into the flexible wire or braided wire in order increase radiopacity. The individual wire elements of the umbrella parts could be connected laterally to adjacent wire elements by seams, swathes, interlacing, through sleeves or rings or rivets. It is advantageous if the individual umbrella strips contain loops or bores to facilitate sewing in the case of umbrella parts that are stitched to one another. Loops that are affixed at the circumference of individual umbrellas can also facilitate the merging of several individual umbrella parts. The use of twisted or braided multiple wires or flexible wires can, in particular, reduces breakage susceptibility and increases flexibility.

The umbrellas or umbrella parts comprising braided wire can, for example, be manufactured by any of the methods of the bobbin lace technique but can also be manufactured mechanically with a braiding machine, especially in the case of simple designs.

In order to increase bio-compatibility, the umbrella structure can also be coated with something like DLC (Diamond-like Carbon), with substances that encourage incorporation or with an antibiotic or thrombotic layer.

In order to seal an umbrella or double umbrella, the device can be provided at one side, preferably however at both sides, with a membrane, a braid, a knitted fabric, a film or other textiles suitable for implantation. The membrane can consist of polyester, PTFE, PVDF, polyurethane, nylon or absorbable materials such as polylactide, cellulose or polydiaxanone, for example, or from fine interlaced wires or braided wires of nitinol or other materials that are absorbable or non-absorbable, or from composite compounds of the materials mentioned above. The membrane can either be stitched in, braided in, pasted on, be pasted to a second membrane or welded on.

When using wire strands, applied threads or fibres from polyester, nylon, absorbable sewing material, cellulose or PTFE can increase the thrombogenicity of the umbrella structures for defect closure.

When looking at the device in the implanted state from above, the outer form of individual umbrellas respectively, depending upon the number and configuration of the strips, can be triangular, quadrangular (e.g., square, rectangular or rhombic), polygonal, star-shaped or continuous (e.g., round, oval or semicircular) in the case of a larger number of strips on the circumference of the outgoing tube.

In order to close an atrial septal defect (ASD), the implantation catheter is, for example, guided into the left vestibule from the femoral vein through the right vestibule over the septal defect. The front umbrella part is, thereafter, reconfigured slowly in the right vestibule by inserting the device and retracting the implantation catheter. The front umbrella part that is almost parallel to the defect at the wall of the left vestibule ensures a secure umbrella fit and prevents this umbrella part from slipping through during retraction. The implantation catheter is thereby advantageously provided with such type of a curvature that it stands perpendicular to the septal wall. Erroneous positioning of the front umbrella at the wrong side of the septum is avoided to a large extent in this manner.

In order to implant the device according to one of the embodiments described above, the same must first be inserted into a catheter, for which purpose it must be elongated. Elongation takes place by extending the device at the front and rear ends. Air bubbles must, subsequently, be removed by flushing out the umbrella system. The elongated device is inserted into the catheter. When the device is pushed out at the target location, it reconfigures itself in the defect in its second state.

The design of the umbrella structures causes the device to centre itself during closure of the defect, which is a great advantage compared to the closing devices of prior art.

A repositioning appliance for exact positioning, whose design is similar to the type of repositioning mechanism of the pull-in aid used, can be provided at one end of the device, preferably at a joint. The repositioning mechanism should act centrally in the middle and not at the outer neck or edge of the umbrella so that this umbrella can be pulled back into the implantation catheter preferably with a catching loop after removing the repositioning mechanism.

If the device comprises tubular wires or flexible wires in the first state, it is of advantage to mount the same at both ends respectively between two annular capillary tubes and join the same in a form-fit manner through sewing, adhesion, soldering or welding. Another capillary tube can then be a part of the repositioning mechanism. The great advantage in using flexible wires is that the forming force at the locations with greater curvature in the second state is considerably less and, therefore, the danger of a wire or strip breaking as in the case of designs that are cut from a metal tube are significantly less.

Loops that are held together in a ring-like structure by means of a circumferential thread through all inner loops can also be affixed at the inner strips instead of an inner tube, a sleeve or a ring.

The individual umbrella parts can also lie flatter against each other and are better protected against wire breakage in the case of long-term stress due to heart contractions. When using wire strands, repercussions of breakage of individual wire filaments on the strength of the overall structure is as good as non-existent.

The repositioning appliance can be in the shape of a ball, for example, in conjunction with a pull-in aid in the shape of modified biopsy forceps that grasps this ball.

Other possible designs for the repositioning device are, for example, a loop for specific gripping devices, a hook, a thread or plastic connector that is separated by a cutting appliance or thermolysis by means of laser energy, a double thread with loop, a screw joint, a bonded joint and a soldered joint that can be released by electrolysis or preferably a coupling that can be released only after removing the inner wire. A groove that facilitates catching of the umbrella end with a catching loop can thereby be worked into the umbrella-sided coupling part as a further security aspect of this umbrella system so that the umbrella can be secured again by means of catheter technology even after final jettisoning.

Thus, an umbrella too can be furnished with outer loops at the periphery through which a circumferential thread is guided, said thread being guided with both its ends through an insertion catheter and permitting the tightening and folding up of the umbrella. The device in accordance with the invention can, therewith, be repositioned and can, advantageously, be pulled back into the insertion catheter in case of incorrect positioning and, if required, be repositioned. This embodiment is applicable for the braided as well as the cut variants.

The latter particularly applies also to tunnel-shaped implants into which a valvular structure from bio materials, absorbable materials or from wire mesh is stitched. The possibility of a trial positioning presents great security advantage that helps avoid possible embolisations and surgical interventions in the case of complications with far-reaching consequences.

At the opposite end of the wire frame, the wire-shaped elements in the case of corresponding embodiments are simply connected to one another by, for example, a ball, wire torsion with or without loops, through soldering, welding, adhesion, wrapping, sewing, by a thread, through a sleeve, through loops or a ring. A second repositioning device such as a loop, for example, with which to receive a guidewire for the "Over-the-Wire-Technique" can, however, also be provided, should the need arise. The device is thereby guided by a wire and can, thus, be positioned more securely and can be simply removed again □ also interventional □ even after disconnection. The wire guide track is removed again in a final step only after completely correct seating of the double umbrella. The wire-shaped elements do not have to be directly connected to one another and can also be indirectly connected by, for example, the umbrella's fabric or by a seam. The advantage here is that reconfiguration of the second umbrella part on one side of the septum takes place slowly in order to avoid abrupt tension release of the device.

In another embodiment of the device in accordance with the invention, the device consists of two umbrella parts of unequal sizes with a broader middle piece in the side view or of a combination of an umbrella part and a plug, or of a spherical outer shape with or without fabric cover so that, functionally, a closure plug, for example, comes into existence for the left cardiac atrium.

In order to close ventricular septal defects, umbrella shapes with an approximately cylindrical middle piece with the diameter of the defect and two outer umbrellas are advantageous. The outer umbrella shape can then also be designed to be oval in order to protect the adjacent valvular structure. A particularly radiopaque marker ring at the upper rim or lower rim of the umbrella would then facilitate position monitoring of the sealing system in the case of implantation. Depending upon the defect to be closed, the cylindrical middle piece can also be designed to be diagonal so that an overall asymmetrical umbrella emerges.

Loops to which individual umbrella parts can be connected by a seam with a thread or wire can be located at the outer rims of the proximal and/or distal umbrella. In the case of this embodiment in which individual flat umbrella parts are connected using seams, it is also beneficial to cut out or press the individual flat umbrella parts from a sheet, manufacture same from a synthetic plate or die-cast the flat umbrella parts from a synthetic material.

In another embodiment of the invention in accordance with the invention, the device consists of two elements without fabric covering that are conical when viewed from the side so that, functionally, a vena-cava umbrella results with which thrombi can be intercepted in order to avoid a pulmonary embolism. In this embodiment it is of advantage to affix small hooks at the side of the umbrella for improved fastening in the vena cava. This umbrella can also be connected in a form-fit manner to a guidewire as a temporary filter for better position correction.

In another embodiment, only the front umbrella part at the tip of the guidewire is covered by a microporous membrane. The lower umbrella part then preferably consists of 2-6 straight strips. The pore size should amount to approximately 0.01 mm. The umbrella system in this embodiment then functions as an embolism protector in connection with interventional measures or as "waste collector" in the case of endoscopic operations in another embodiment.

The device in accordance with the invention serves as a plug in another embodiment if the device is designed as a cylinder in the second state. The repositioning portion can thereby be sunk advantageously into the umbrella in order not to inadvertently hook itself in the case of further catheter application.

In another embodiment, the device in accordance with the invention can be provided with a repositioning mechanism on both sides. This is an advantage especially for the implantation of umbrellas that are dissimilar in size so that each umbrella can be implanted securely from the venous as well as from the arterial side, corresponding to the anatomic conditions. Also, the umbrella parts can each be slowly reconfigured at the defect wall from both sides of the defect in the context of a loop procedure.

In another embodiment of the device in accordance with the invention, one or both umbrellas can respectively exhibit a hole with a defined diameter between the strips and the umbrella membrane for a situation in which the defect is not to be closed completely and a defined residual flow is desired through the defect. A plug with a defined lumen can also be used for flow reduction in the case of vessels. A valvular structure can, if required, also be integrated in this lumen in order to prevent return flow.

The same materials can be used in these alternative embodiments as are used in the other embodiments. It is only in the second state that the lateral shape is designed differently.

The umbrella frame of the device in accordance with the invention can be completely covered by a fabric, a netting or a foil in the form of a double umbrella or only one of the umbrella parts can be covered inside and/or outside. Moreover, parts of the umbrella can be furnished with thrombogenic threads or the complete umbrella frame can be embedded in foam. Materials that could be used would, for example, be: PETP (polyethylene glycol terephthalate, e.g. Dacron™), polyimide (e.g. nylon), PTFE (polytetrafluoroethylene, e.g. Teflon™), silk, deoxygenated cellulose, absorbable plastic (e.g. polylactide, polydioxanone (e.g. PDS™) as well as fabric, microporous polyurethane foils, flexible wire mesh made from thinnest steel or nitinol wire or combinations of materials mentioned. Polyurethane foam and polyvinyl foam (e.g. Ivalon™), for example, are suitable for foam embedding. The fabric cover can be fastened to the umbrella frame through loops that are affixed to the strips or connecting points by sewing, wrapping, compression moulding, adhesion, welding, soldering, shrink-fit or dip-coating. If the umbrella frame is made from a loosely braided wire strand, the fabric cover can be fastened simply by whip stitching the tabs of the flexible wire formed by the individual wires. A braiding together with neighbouring strips in sub-areas is advantageous in the case of braided strips for which purpose braided-in loops can also be provided.

The overall thickness of the wire strand amounts to 0.01-0.06 mm, preferably 0.02-0.35 mm. The minimal implantation catheter diameter amounts to 3-9 F (1-3 mm).

The device in accordance with the invention can be used to close an atrial septal defect (ASD), a ventricular septal defect (VSD), a patent ductus arteriosus botalli (PDA) or an arteriovenous malformation, for example, whereby the embodiments comprising connected wire-shaped or strand-shaped elements at both ends are particularly suited to closure of large PDA, VSD and arteriovenous malformations. It can also find vena caval application in a special embodiment to intercept thrombi or be used as an implantable restriction plug or flap valve with a defined lumen for flow reduction in which case lateral affixing of the repositioning device is expedient.

The invention will now be explained by means of a few illustrations. It is understood that the individual elements and embodiments can also be respectively combined with one another wherever possible and expedient.

FIG. 1 presents a side view of a tubular embodiment of the invention with an implant with strips of respectively equal length in an elongated state.

FIG. 1a presents a magnified view of a section of the slit tube.

FIGS. 2 and 3 illustrate the manner in which the implant of an embodiment in accordance with FIG. 1 as a double umbrella behaves when being pushed out from a catheter and during subsequent disconnection.

FIG. 2 presents a side view of the embodiment according to FIG. 1 in a catheter with a partially reconfigured double umbrella.

FIG. 3 presents a side view of the embodiment according to FIG. 1 with a disconnected, completely reconfigured double umbrella with respectively equal-sized diameters of the proximal and distal umbrella with a narrow middle piece.

FIG. 4 is a frontal view of the front umbrella part in a reconfigured state with strips of equal length according to FIG. 3.

FIG. 5 presents another embodiment of the completely reconfigured double umbrella according to FIG. 1 with a broader middle piece and a large proximal umbrella and a smaller distal umbrella.

FIG. 6 is a frontal view of the front umbrella part according to FIG. 5 in a reconfigured state with strips of partially different lengths corresponding to the respective umbrella diameters.

FIGS. 7a-g present the top view of the differently shaped strips of the tubular embodiment according to FIG. 1 or 5.

FIGS. 8a-g again present different design possibilities of strips with holes or grooves.

FIGS. 9a-g illustrate the different design possibilities of the connecting elements between the individual strips.

FIGS. 10a-g present more of the different design possibilities of connecting elements between individual strips.

Figure 1:
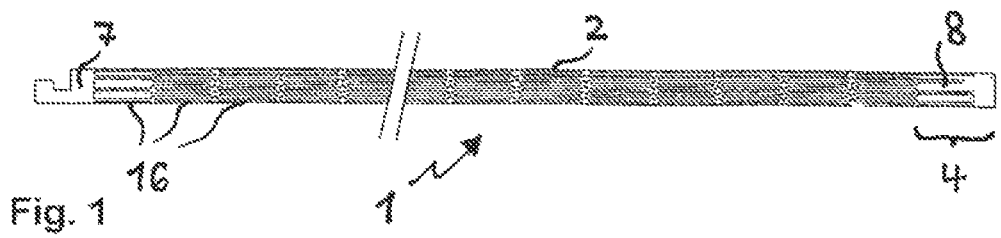
Figure 20:
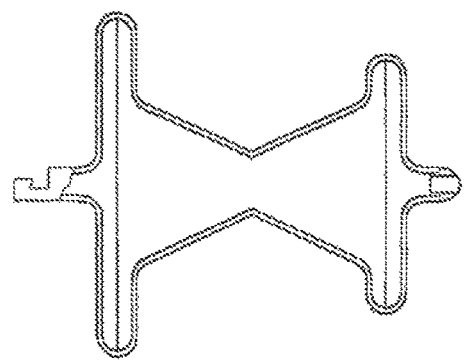

FIG. 20 presents a cross-section of the embodiment according to FIG. 1 with a double cone shape, without a front tip and with a sunk-in connector.

Figure 21:
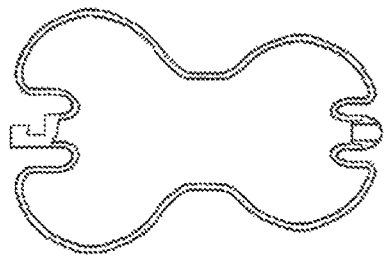

FIG. 21 presents a cross-section of the embodiment according to FIG. 1 with a double spherical outer shape and with a cylindrical middle piece.

Figure 22:
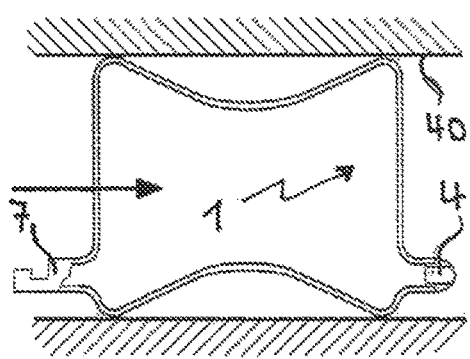

FIG. 22 presents a cross-section of the embodiment according to FIG. 1, with the shape of a restrictor.

Figure 23:
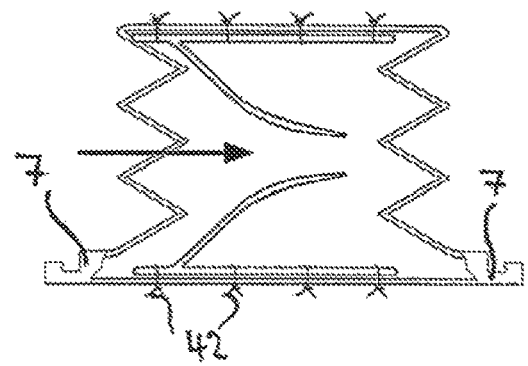

FIG. 23 presents a cross-section of the embodiment according to FIG. 1, with a cylindrical outer shape as a valve-bearing frame.

Figure 24:
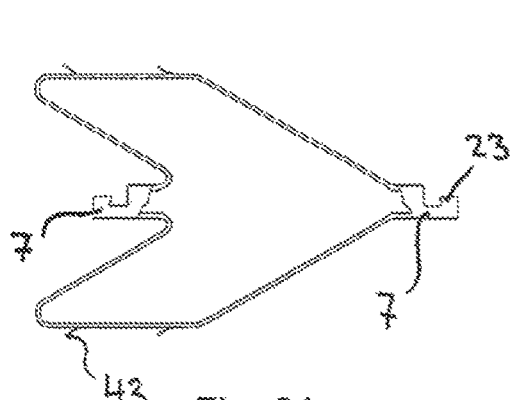

FIG. 24 presents a cross-section of the embodiment according to FIG. 1, with a conical and a cylindrical part that has hooks.

Figure 25:
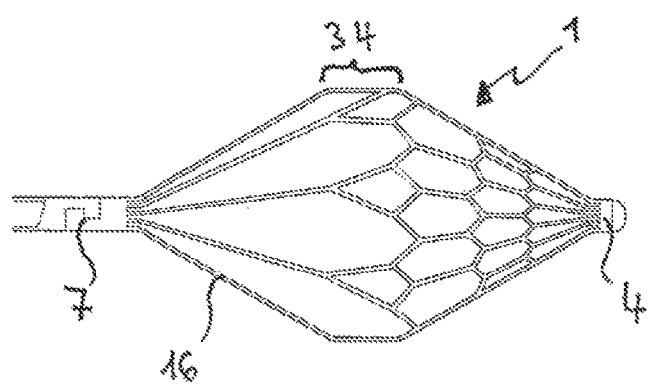

FIG. 25 is a side view of the embodiment according to FIG. 1, with a double cone shape and a cylindrical part.

Figure 26:
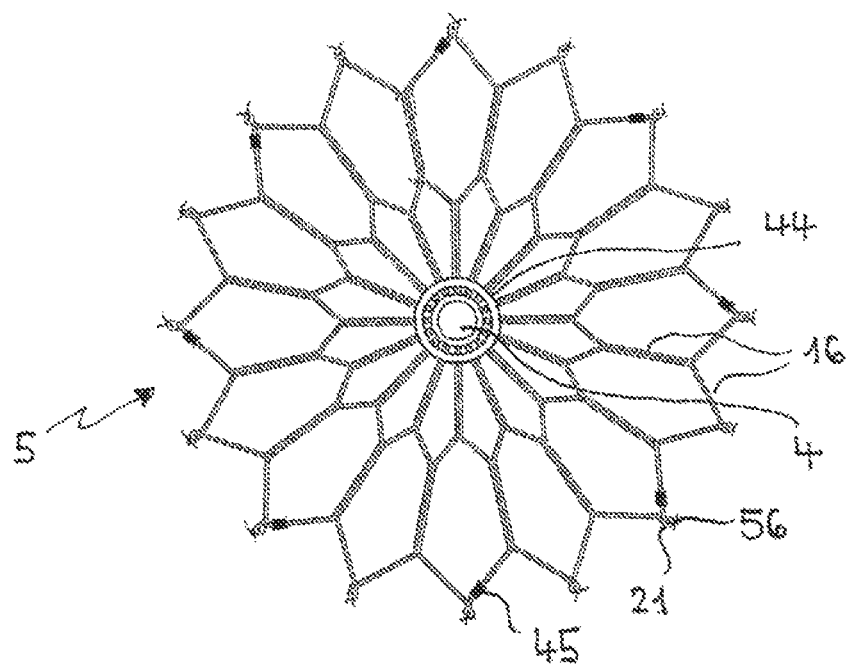

FIG. 26 presents a frontal view of the front umbrella part according to FIG. 1 in a reconfigured state with strips of varying lengths that are braided or wound with several individual wires.

Figure 27:
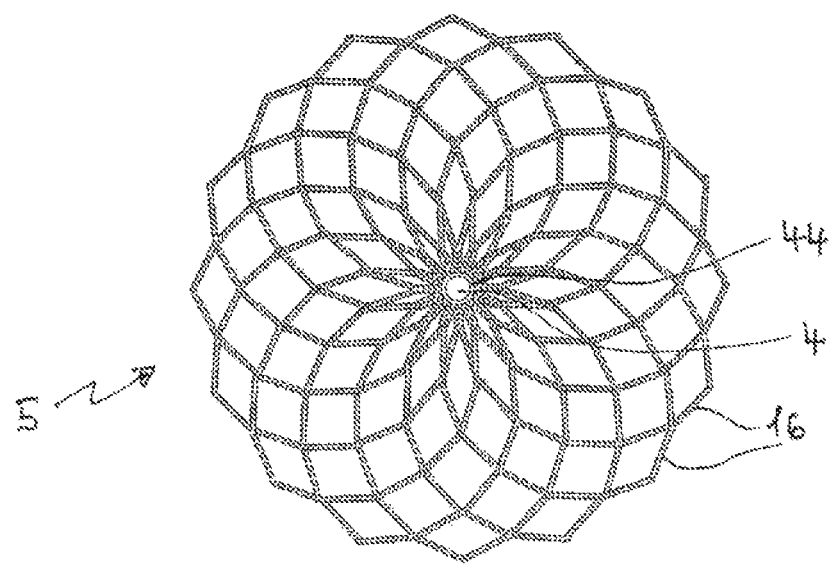

FIG. 27 presents a frontal view of the front umbrella part according to FIG. 1 in the reconfigured state with wound strips of equal length.

FIGS. 28a-g present different embodiments of the braided, wound or strand-shaped strips of an embodiment according to FIG. 26 or 27.

FIGS. 29a-f present different embodiments of the braided, wound, or strand-shaped strips of an embodiment according to FIGS. 26 or 27.

FIGS. 30a-f present more of the different design possibilities of connecting elements between the individually wound or braided strips.

Figure 31:
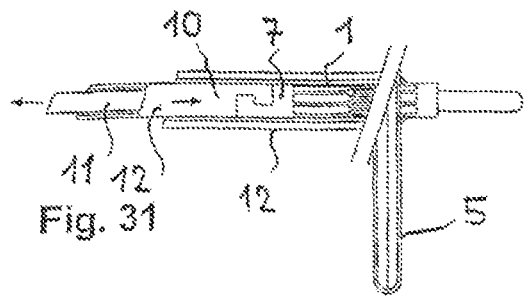

FIG. 31/32 are side views of implant disconnection according to FIG. 1, with a coupling.

Figure 33:
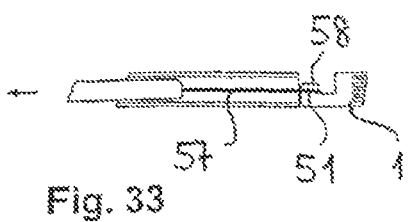

FIGS. 33/34 are side views of implant disconnection using a sling.

Figure 35:
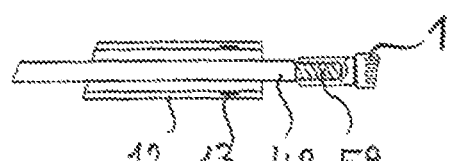

FIGS. 35/36 are side views of implant disconnection with a screw joint.

Figure 37:

FIGS. 37/38 are side views of implant disconnection using forceps.

Figure 39:
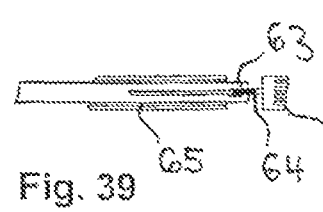

FIGS. 39/40 are side views of implant disconnection using a gripper.

Figure 41:
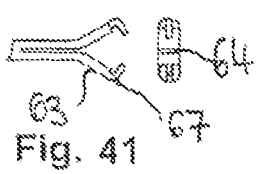

FIG. 41 presents a side view and a frontal view of the gripper.

Figure 42:
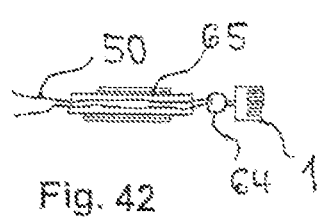

FIG. 42 is a side view of an implant that has been connected by sutures.

Figure 43:
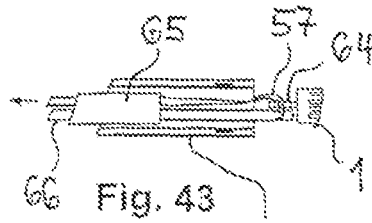

FIGS. 43/44 present side views of implant disconnection with a sling combined with a counter-wire.

Figure 45:
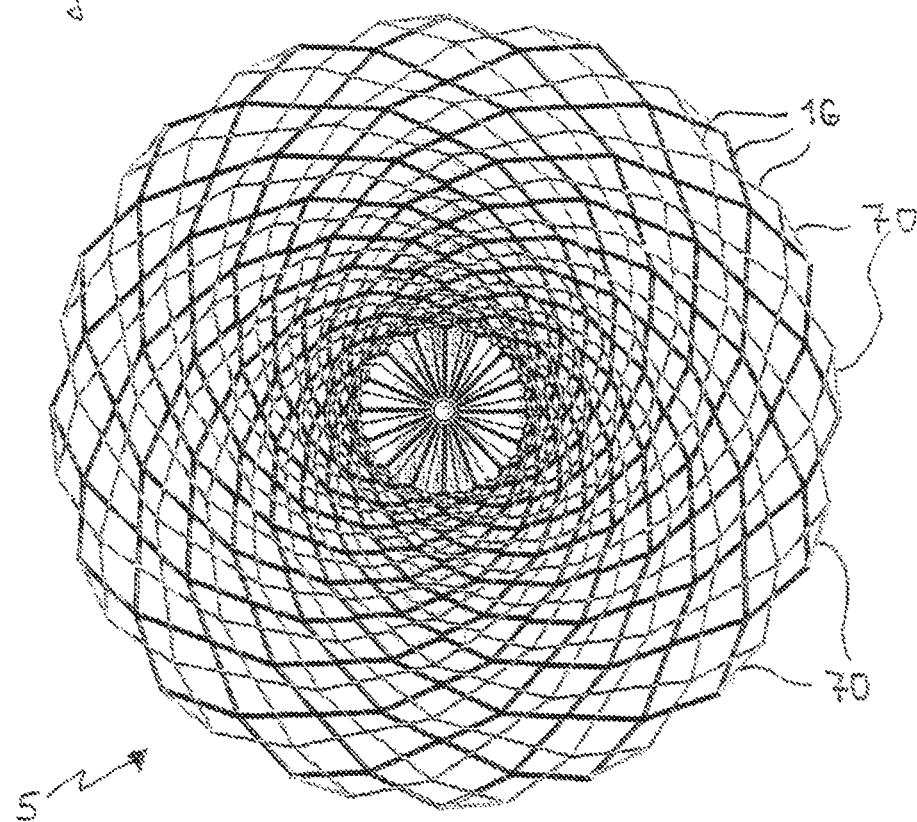

FIG. 45 illustrates a top view of an umbrella that has been cut from a tube with strips that run diagonally at the periphery in order to alleviate tension.

Figure 46:
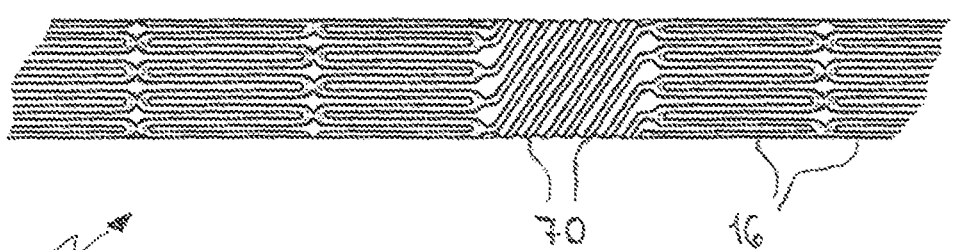

FIG. 46 illustrates a cut section of the tube in a first state with strips that run diagonally parallel in order to alleviate tension.

Figure 47:
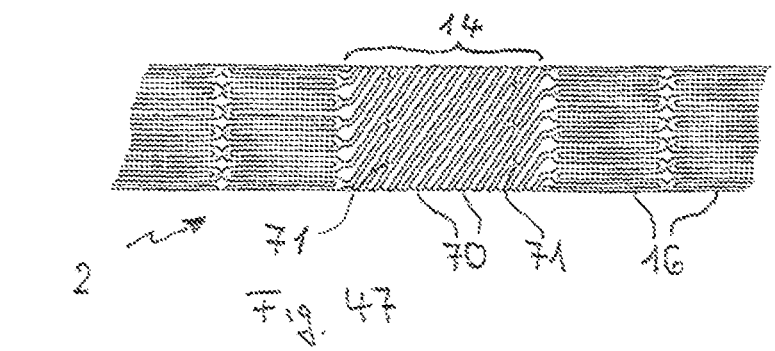

FIG. 47 presents a tube section with strips that run diagonally parallel in the middle piece for self-centring.

Figure 48:
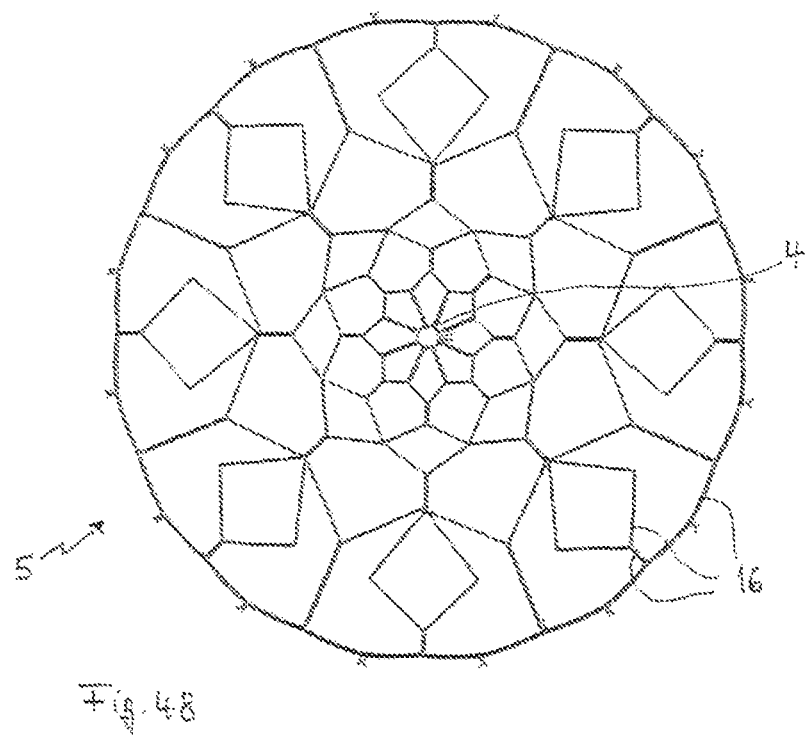

FIG. 48 is a top view of an umbrella braided from metallic flexible wires in which the central rhombi are connected by loops and a thread.

Figure 49:
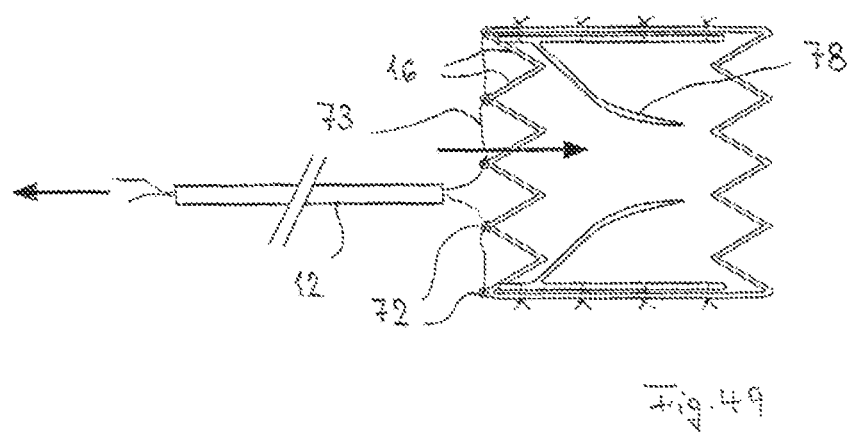

FIGS. 49/50 is a repositionable variant of the embodiment in FIG. 23 of a valvular structure.

The individual illustrations are described in greater detail below.

FIG. 1 presents a side view of an embodiment of the device in accordance with the invention in the form of a slit tube 2 in a first elongated state.

In this design of implant 1, all strips 16 are of equal length respectively. Broader strips are located at the proximal end piece 4 and less broad strips 16 are located at the circumference in order to reduce rigidity of implant 1 in areas with great curvature in a second state after thermal recasting. An implant coupler 7 is located at the distal end.

Figure 1A:
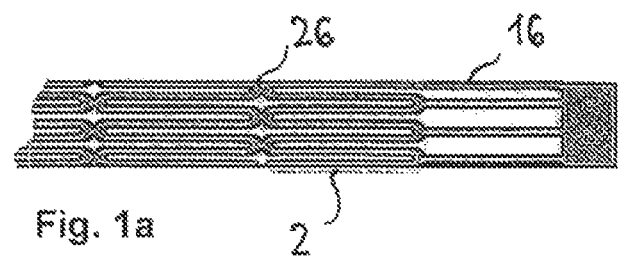

FIG. 1a presents a magnified view of a section of the tube 2 that is slit as in the case of stents with strips 16 of equal size which are respectively alternately connected laterally to one another in this embodiment with X-shaped connecting elements 26. Strips 16 that run parallel to one another respectively form a (tube) segment.

Figure 2:
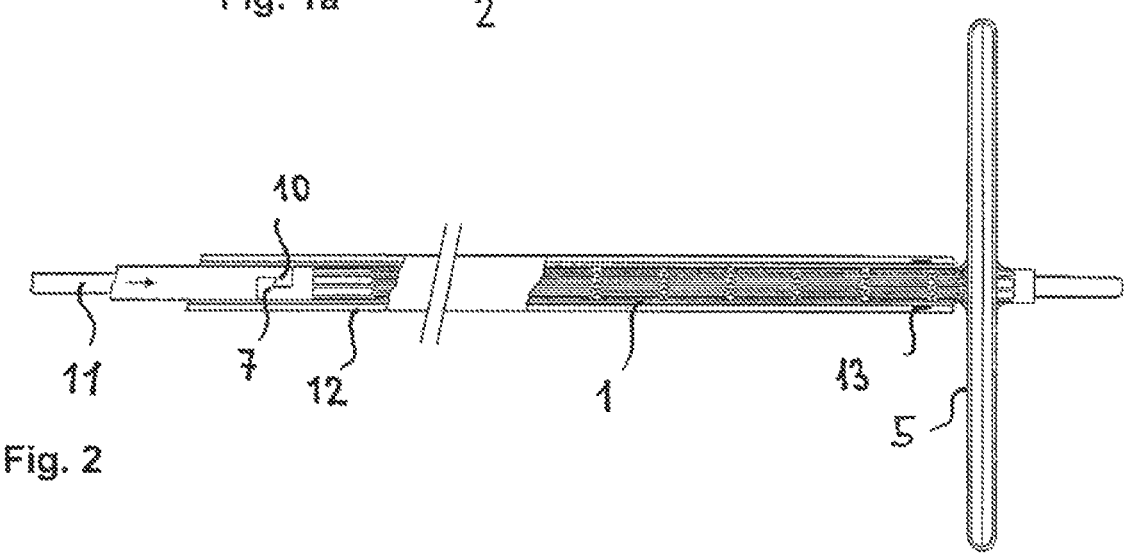

FIG. 2 presents a side view of implant 1 with a completely reconfigured proximal umbrella 5 outside of the insertion catheter 12. Implant 1 that is elongated in insertion catheter 12 is hooked into the pusher coupler 10 at the distal end with its implantation coupler 7 and is fastened to pusher 9 by an inner guidewire 11. Insertion catheter 12 has a marker ring 13 at its proximal end.

Figure 3:
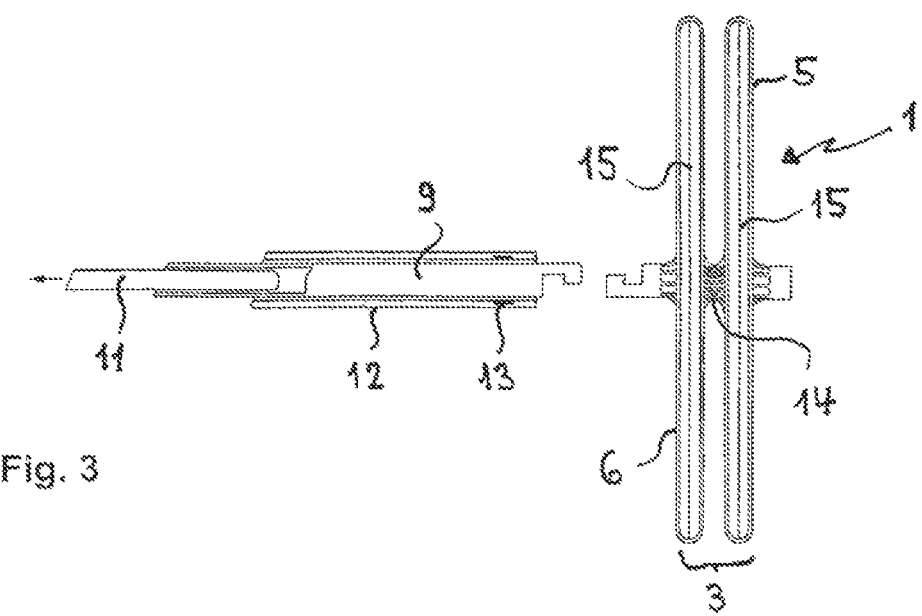

FIG. 3 presents a side view of a disconnected implant 1 according to FIG. 1 in an embodiment that has a double umbrella 3 in which the proximal umbrella 5 and the distal umbrella 6 each have a respective diameter of the same size. A narrow middle piece 14 is located between the two. A membrane 15 for improved closing of defects is located in the proximal umbrella 5 and distal umbrella 6. The pusher coupler 10 is located outside of the insertion catheter 12. Implant 1 with implant coupler 10 was disconnected from pusher 9 by retracting the guidewire 11 in the pusher 9. A marker ring 13 is located at the end of the insertion catheter 12.

Figure 4:
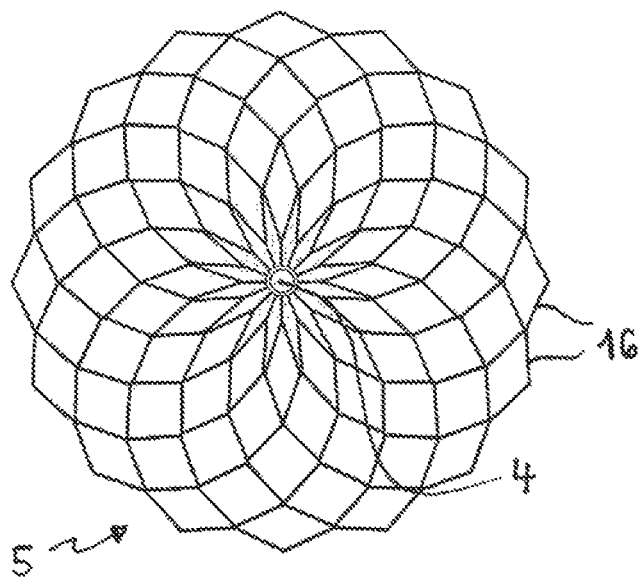

FIG. 4 presents a frontal view of the implant 1 according to FIG. 3 in the shape of a double umbrella that is manufactured from a tube which is slit 32 times by thermal treatment in the illustrated embodiment. The front and rear parts of the proximal and distal umbrellas are each formed from 32 strips at the circumference. The breadth of the umbrella in the case of this embodiment comprises 7 strip lengths respectively. The required overall length for the slit tube 2 for this implant 1 in the shape of a double umbrella 3, therefore, amounts to four times the 7-fold length of a strip, corresponding to 28 times the length of an individual strip+the length for the proximal end piece 4+the length for the distal end with the implant coupler 7+the middle piece 14.

In this embodiment with strips 16 of respectively same lengths, the strips used for the umbrella parts form quadrangular rhombi amongst themselves. In order to increase flexibility in areas with large forming forces at the proximal end piece 4 and the implant coupler 7, the breadth of the individual strips or the rigidity can be reduced by longitudinal holes, the wall thickness can be thinned by electropolishing or the number of strips can be reduced. In order to increase flexibility and spring characteristics of the double umbrella, it is also expedient to reduce the breadth of the individual connecting elements or reduce wall thickness with structural measures.

Figures 5, 6:
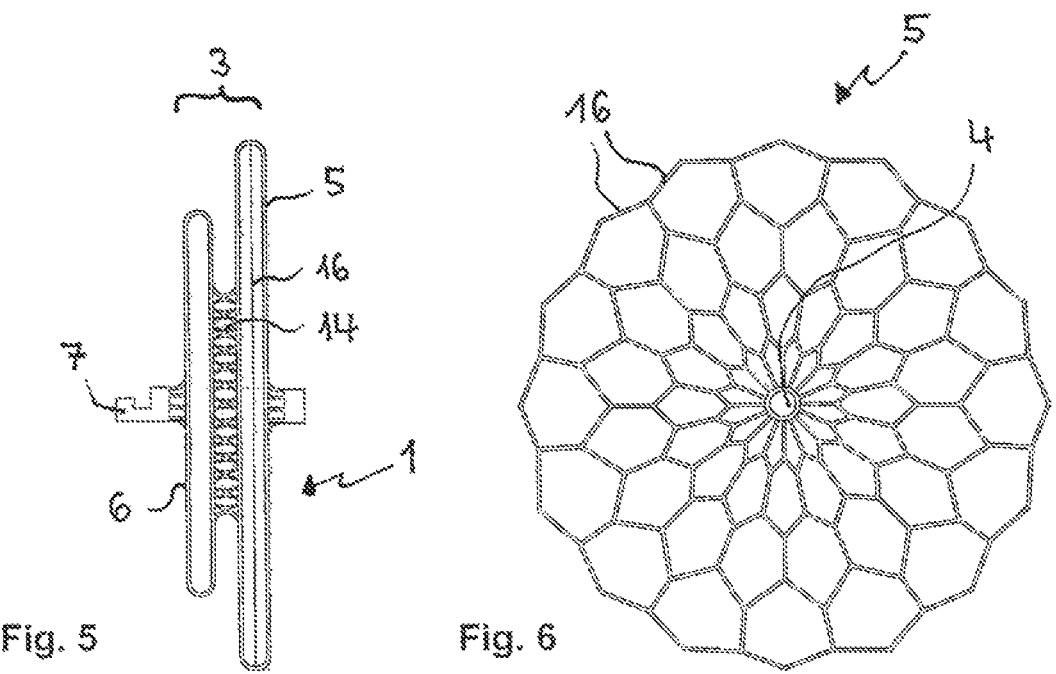

FIG. 5 presents a side view of implant 1 according to FIG. 1 in another embodiment as a double umbrella 3 with unequal diameters of the proximal and distal umbrellas. The proximal umbrella 5 in this embodiment has a greater diameter than the distal umbrella 6. A broad middle piece 14 is located between them. Membrane 15 for better closing of defects is located in proximal umbrella 5.

FIG. 6 is a frontal view of the double umbrella according to FIG. 5. It is also manufactured from a 32-fold slit tube in this embodiment. The front and rear part of the proximal and distal umbrella are respectively formed at the circumference from 32 strips and the umbrella breadth in this embodiment respectively comprises 8 strip lengths.

In the case of this embodiment with strips 16 of respectively different lengths, depending upon the distance to the centre of the umbrella with the proximal end piece 4, strips 16 used in the case of umbrella parts, form hexagons amongst themselves.

FIGS. 7a-g respectively present designs of a strip 16 with a constant breadth, with a conical tapering breadth (7b), with a cone-shaped thickening 17 in the central part (7c), with a reduction of the strip breadth in the central part (7d), with a curve (7e), with an S-shaped curve (7f) and with a diagonal progression (7g).

FIGS. 8a-g respectively present designs of a strip 16 with the same breadth and four loops, with a continuous longitudinal slot (8b), with 3 longitudinal slots (8c), with four enlargements in which a loop is respectively located (8d), with two constrictions in which a loop is respectively located (8d), with two constrictions with an enlargement that lies in between in which three loops are located (8e), with two constrictions with an enlargement in the middle as in the case of FIG. 8e (80, and with four enlargements, however without loops, as in FIG. 8d (8g).

FIGS. 9a-g respectively illustrate connecting elements of two narrow strips with a broad strip 16, of two narrow strips with a broad strip 16 in which a lateral curve of the narrow strips is alleviated by a groove on both sides (9b), a fork-shaped connecting element between two narrow strips with a third equally narrow strip (9c), a C-shaped connecting element between two narrow strips with an equally narrow third strip (9d), a fork-shaped connecting element between three narrow strips with a fourth equally narrow strip (9e), a candelabra-shaped connecting element between four narrow strips with an equally narrow fifth strip (9f) and a three-fold fork-shaped connecting element between four narrow strips that are first connected to one another in pairs before the two individual strips are then again connected to a fork-like connecting element with an equally narrow seventh strip 16 (9g).

FIGS. 10a-g illustrate an H-shaped connecting element between strips that are respectively located pair-wise, an X-shaped connecting element between strips that are respectively located pair-wise, whereby a lateral curving of the strips is facilitated by grooves on both sides (10b), a connecting element that is formed from two C-shaped connecting elements lying opposite each other with an intermediate short strip (10c), a curved connecting element between two strips respectively located pair-wise (10d), an S-shaped connecting element between two strips respectively located pair-wise (10e), a connecting element that comprises two opposite candelabra-shaped connecting elements between which a short straight strip is located (10f) and another embodiment of a connecting element which consists of two opposite fork-shaped connecting elements with four strips respectively between which a loop is located (10g).

FIGS. 11 to 24 present a side view/silhouette of different embodiments of implants, in accordance with the invention.

Figure 11:
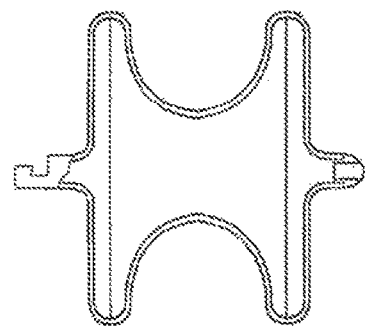
FIG. 11 is a side view of the embodiment according to FIG. 1 with a double umbrella that has a curved middle piece.

FIG. 11 is a side view of implant 1 according to FIG. 1 in a design as a double umbrella with a curved middle piece. The proximal umbrella and distal umbrella each have an inner membrane and are each of the same size. The proximal end piece and the implant coupler are respectively manufactured to be hollow and thus permit implantation by an inner guidewire as in FIG. 2.

Figure 12:
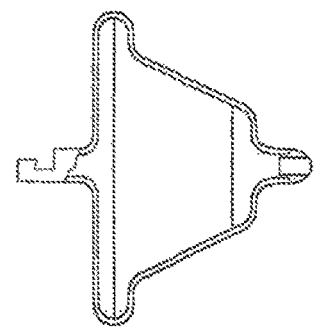
FIG. 12 is a side view of the embodiment according to FIG. 1 with a rear umbrella part and a conical middle piece.

FIG. 12 presents a side view of implant 1 according to FIG. 1 which has been shaped into a spherical umbrella structure using thermal treatment, with a distal umbrella that has an inner membrane. The implant coupler is located in the centre of the distal umbrella. The proximal end piece is located centrally in front at the implant.

Figure 13:
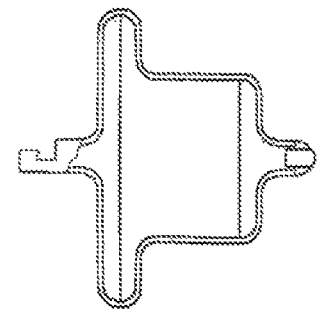
FIG. 13 is a side view of the embodiment according to FIG. 1 with a rear umbrella part and a cylindrical middle piece.

FIG. 13 is a side view of the embodiment according to FIG. 1 with a distal umbrella that has an inner membrane and a cylindrical middle piece. The implant coupler is located in the centre of the distal umbrella. The proximal end piece is located centrally in front at the implant.

Figure 14:
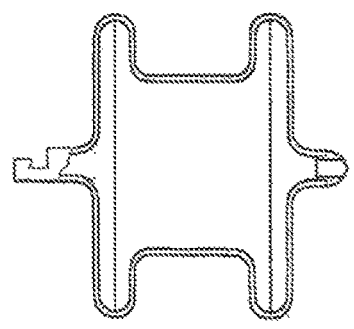
FIG. 14 is a side view of the embodiment according to FIG. 1 with a double umbrella that has a cylindrical middle piece.

FIG. 14 presents a side view of the implant 1 according to FIG. 1 in an embodiment as a double umbrella with a cylindrical middle piece. The proximal umbrella and the distal umbrella respectively have an inner membrane and are each of the same size. The implant coupler is located in the centre of the distal umbrella. The proximal end piece is located centrally in front of the implant.

Figure 15:
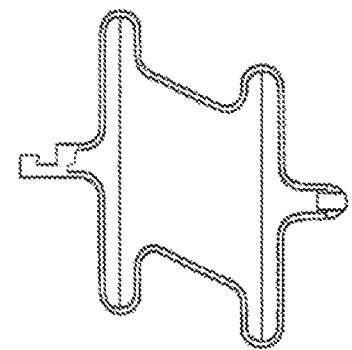
FIG. 15 is a side view of the embodiment according to FIG. 14 with a double umbrella that has a diagonal, cylindrical middle piece.

FIG. 15 presents a side view of a double umbrella as does FIG. 14, however with a diagonal, cylindrical middle piece. The proximal umbrella and the distal umbrella each have an inner membrane and are each of the same size. The implant coupler is located in the centre of the distal umbrella. The proximal end piece is located centrally in front of the implant. Due to the diagonal middle piece, the imaginary axis of the implant coupler is offset laterally to the proximal end piece corresponding to the slant.

Figure 16:
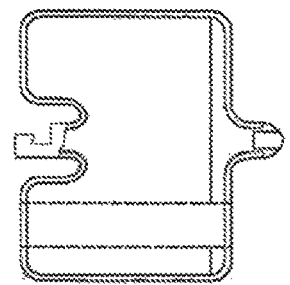
FIG. 16 is a side view of the embodiment according to FIG. 1, with a cylindrical umbrella structure.

FIG. 16 is a side view of the embodiment according to FIG. 1, with a cylindrical umbrella structure. The implant coupler is located in the centre of the distal umbrella. The proximal end piece is located centrally in front of the implant. Apart from an inner membrane, a channel too runs through the implant in order to, for example, permit residual blood to flow through this channel.

Figure 17:
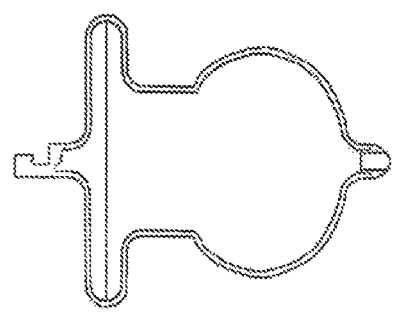
FIG. 17 is a side view of the embodiment according to FIG. 1 with a spherical outer shape in the front, a cylindrical middle piece and a distal umbrella.

FIG. 17 presents a side view of an implant 1 according to FIG. 1, presents a side view of an implant in the shape of a double umbrella with a proximal spherical umbrella structure, a cylindrical middle piece and a distal umbrella with an inner membrane. The implant coupler is located in the centre of the distal umbrella. The proximal end piece is located centrally in front of the implant.

Figure 18:
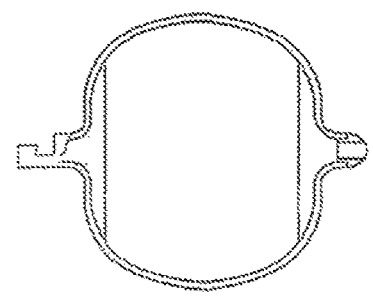
FIG. 18 is a side view of the embodiment according to FIG. 1 with a spherical umbrella structure.

FIG. 18 presents a side view of an implant 1 according to FIG. 1 with a spherical umbrella structure and two inner membranes. The implant coupler is located in the centre of the distal umbrella. The proximal end piece is located centrally in front of the implant.

Figure 19:
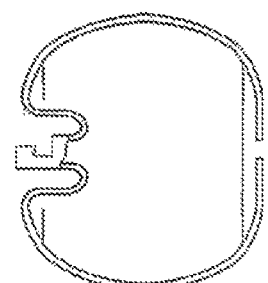
FIG. 19 is a side view of the embodiment according to FIG. 18, with a spherical outer form without a front tip.

FIG. 19 is a side view of another spherical umbrella structure according to FIG. 18 with an inner membrane, however with an inner implant coupler lying in the spherical umbrella structure in order to reduce the risk of injury. Only one opening 38 is, however, located proximally in the centre of the spherical umbrella structure without a proximal end piece with which to receive a guidewire.

FIG. 20 presents a cross-section of an embodiment of the implant according to FIG. 1 in the shape of a double umbrella with a double cone umbrella structure, with a smaller proximal umbrella and a larger distal umbrella with an inner membrane. The implant coupler is located in the centre of the distal umbrella. The proximal end piece is located centrally in front of the implant.

FIG. 21 is a cross-section of another embodiment of the implant according to FIG. 1 in the shape of a double umbrella with a proximal smaller spherical umbrella structure and a distal larger spherical umbrella structure with inner membranes. The implant coupler is located in the centre of the distal umbrella. The proximal end piece is located centrally in front of the implant.

FIG. 22 is a cross-section of implant 1 with an inner hollow design according to FIG. 1, with a double cone umbrella structure with which to reduce flow in vessels. In the case of this design of the implant, the proximal end piece and the distal implant coupler are preferably located laterally close to the vascular wall in order not to additionally impede blood flow.

FIG. 23 presents a cross-section of a cylindrical umbrella structure according to FIG. 1 that is hollow inside and in which a valve-bearing structure has been sewed in with, here, four seam joints respectively in the longitudinal direction of implant 1 as a valve substitute in the vessels. In the case of this embodiment of the implant, an implant coupler 7 is preferably laterally located proximally and distally respectively in order to facilitate implantation from both sides depending upon the desired valve function and flow direction.

FIG. 24 presents a cross-section of another embodiment of a temporary implant 1 according to FIG. 1 as a so-called cava umbrella with a proximal conical umbrella structure, a cylindrical middle piece at which lateral hooks for fastening can be located. An inner implant coupler is located at the distal end. An implant coupler with a groove 23 is also located at the proximal end in order to also facilitate proximal interventional recovery of the temporary implant with a catching loop.

FIG. 25 is a side view of an embodiment of a temporary implant 1 in the form of a "protection device" according to FIG. 1 with a conical umbrella structure and a cylindrical part that is proximally covered on the outside by a micro-perforated membrane in order to, for example, intercept micro-embolisms. Implant 1 should thus lie adjacent to the vascular wall.

The cylindrical middle piece 34 is connected to the implant coupler 7 by straight strips 16. These are, however, not covered by a membrane. This protection device can also be firmly fixed to a pull-in aid, if required.

FIG. 26 presents a proximal view of an embodiment of the implant 1 in the shape of a double umbrella 3 with an illustration of the front side of a proximal umbrella 5. In the case of this variant in accordance with the invention, the entire implant comprises strips of varying lengths that have been braided or wound from several individual wires. Braided or wound strips 16 in the centre of the proximal umbrella 5 are integrated with a sleeve 44 at the proximal end piece 4. The breadth of the umbrella in this embodiment is formed by an overall length of respectively four strips 16. In this connection, eight radiopaque markers are affixed at the outer rim of the proximal umbrella in order to simplify umbrella positioning with X-ray control. Loops 21 with which individual umbrella parts can be connected by a thread or wire to a seam 56 can also be located at the outer rims of the proximal and distal umbrellas. In an embodiment in which the individual flat umbrella parts are connected by seams, it is also an advantage to cut out or die-cut the individual flat umbrella parts from a sheet, manufacture same from a plastic plate or to injection mould the flat umbrella parts from plastic.

FIG. 27 is a front view of an embodiment of the implant 1 in the shape of a double umbrella 3 as in FIG. 4 with an illustration of the front side of a proximal umbrella 5. In this variant in accordance with the invention, however, the entire implant comprises strips 16 of the same length that have either been braided or wound with several individual wires. In the centre of the proximal umbrella 5, the braided or wound strips 16 are connected to a sleeve 44 of the proximal end piece 4. The breadth of the umbrella in this embodiment is formed by an overall length of seven strips 16 respectively.

FIGS. 28a-g illustrate various strips 16 that consist of braided wires in a simple embodiment (28a), of a wound wire strand of several individual wires whereby it is especially advantageous to manufacture at least one individual wire of the wire strand from a radiopaque material (28b), of two individual wires that are wound around one another (28c), of two individual wires with a longitudinal slot that are twisted around one another (28d), of two individual wires that are wound around one another, thereby forming two loops (28e), of two individual wires that are wound around one another as in FIG. 28e, wherein, however, several longitudinal slots are designed instead of loops (28f) and of two braided wires with two lateral loops (28g).

FIGS. 29a-f present wrapped connections between two individual wires in a short form (29a), a long wrapped connection between two individual wires (29b), a long wrapped connection between two individual wires as in the case of FIG. 29b, however thrombogenic sutures are also braided in the wrapped connection (29c), a braided connection of a strip that is connected by two wrapped connections to two individual wires respectively (29d), a braided connection between three strips that are each equally broad (29e) and a braided connection between two strips that are equally broad and a third strip whose breadth tapers conically (29f).

FIGS. 30a-f illustrate a nodal connection between four individual wires (30a), a braided connection between four equally broad, braided strips (30b), a connection between two wire strands with a locking sleeve (plastic threads can also be used instead of wire strands (30c), a connection between two wire strands with a wrapping (30d), a riveted joint between two strips of braided wires (in the case of strips made from monofilament or multifilament plastic it is also possible to weld intersecting strips together) (30e) and a seam between two strips of braided wires that have loops as in FIG. 28g (30f).

FIG. 31 presents a side view of the procedure for implantation of an implant through an insertion catheter 12. For this purpose, the elongated implant 1 with an implant coupler 7 is hooked into the pusher coupler 10 and fastened by an inner guidewire. Implant 1 is consequently reversibly connected to pusher 9. The elongated implant 1 is pushed by guidewire 11 with pusher 9 and reconfigures itself partially at first to the proximal umbrella 5 upon exiting the insertion catheter 12. An inner marker ring 13 at the proximal end of the insertion catheter 12 serves as a hypomochlion when retracting the reconfigured parts of implant 1 into the insertion catheter 12 in the case of incorrect positioning. It also facilitates orientation using X-ray control. The distal umbrella is also completely reconfigured outside the insertion catheter upon further advancement of the pusher.

Figure 32:
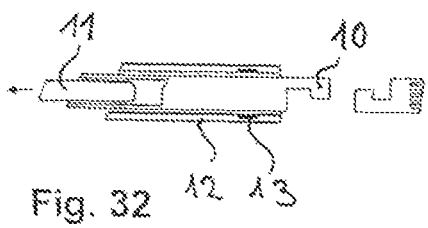

FIG. 32 is a side view of the decoupling of an implant 1 according to FIG. 31. The pusher coupler 10 must be located outside the insertion catheter 12. Only then can implant 1 with the implant coupler 10 1 be permanently disconnected from the pusher coupler 10 at the proximal end of pusher 9 by retracting the guidewire 11 into the pusher 9. A marker ring 13 at the end of the insertion catheter 12 facilitates position control with radiography.

FIG. 33 is a side view of an implant 1 fastened at a sling 57 by tensioning (refer arrow) the pull-in aid. For fastening, the head of sling 51 thereby grasps a hook 58 or engages with the groove 23 of an implant coupler 7 at the distal end of the implant 1.

Figure 34:
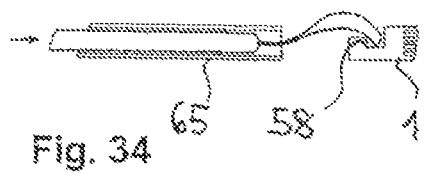

FIG. 34 presents a side view of a disconnected implant 1 with a hook 58 at the distal end of the hook-shaped implant coupler. By advancing sling 51 in the pull-in aid 65, the sling that is being tensioned is released from the pull-in aid and releases the implant. A long double thread can also be used as a sling substitute as an alternative to the sling.

FIG. 35 illustrates a side view of a screw joint between an implant 1 that has a bushing at is distal end and a long wire strand 48 that has a screw thread 59 at its proximal end. Implant 1 that is fastened to the wire strand 48 is pulled out of insertion catheter 12. A marker ring 13 at the insertion catheter 12 facilitates position control with radiography.

Figure 36:

FIG. 36 is a side view of a disconnected implant 1 that has a bushing 60 at its distal end. The wire strand 48 with the screw thread 59 is screwed out of the bushing 60 of implant 1 by means of an anti-clockwise rotation and the implant is released. The wire strand 48 is subsequently pulled back into the insertion catheter 12. An inner marker ring 13 is located at the end of the insertion catheter 12.

FIG. 37 is a side view of an implant 1 that is connected using forceps and that has a connecting ball 62 at its distal end which will be grasped by long forceps 61. The forceps 61 are pushed out of the insertion catheter 12 with the fastened implant 1. A marker ring 13 at the end of the insertion catheter 12 facilitates position control with radiography.

Figure 38:
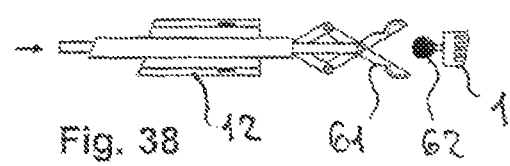

FIG. 38 presents a side view of implant 1 disconnection using forceps. By opening forceps 61, the connecting ball 62 is released at the distal end of the implant. An inner marker ring 13 is located at the end of insertion catheter 12.

FIG. 39 is a side view of an implant 1 that is connected using a gripper and that has a grip screw 64 at its distal end which is held firmly by the gripper jaws of a long gripper 63. The two gripper jaws 67 of the gripper 63 are prevented from opening by the pull-in aid 65 surrounding it.

Figure 40:
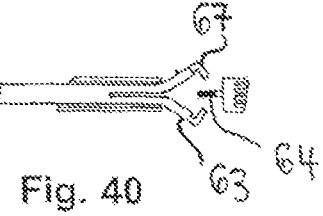

FIG. 40 presents a side view of implant 1 disconnection using a gripper. By advancing the gripper 63 in the pull-in aid 65, the gripper jaws 67 can open after exiting the pull-in aid 65 due to material-related re-set forces and release the grip screw of implant 1 again.

FIG. 41 illustrates a side and frontal view of the gripper 63 with its two gripper jaws 67 in a preferred embodiment.

FIG. 42 is a side view of an implant 1 connected with a suture. The implant 1 that has a grip screw 64 at its distal end is, thereby, fastened to both threads by tensioning a double thread 50 at a pull-in aid 64. By extracting a thread 50 outside the insertion catheter 12, implant 1 can be released after extracting half the thread length.

FIG. 43 is a side view of an implant 1 connected to a sling 57 in combination with a counter-wire 66. Implant 1, that has a grip screw 64 at its distal end, is fastened to a tensioned sling 57 that runs with both wires through the grip screw 64, by looping the counter-wire. Sling 57 and the counter-wire are guided through a pull-in aid 65 and are pushed through an insertion catheter 12 till implant 1 is located outside the insertion catheter 12. A marker ring 13 at the end of the insertion catheter 12 facilitates position control using radiography.

Figure 44:
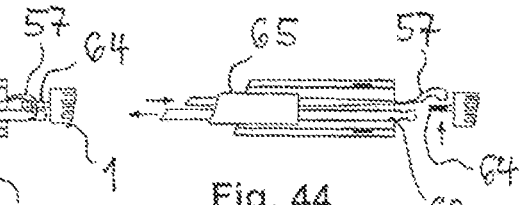

FIG. 44 presents a side view of an implant 1 disconnected with a sling 57 in combination with a counter-wire 66. After checking correct positioning of implant 1, the sling 57 is pushed slightly forward through the pull-in aid 65 so that looping of the counter-wire 66 eases and the counter-wire 66 can then be pulled back into the pull-in aid 65. In doing so, sling 57 slides out of the grip screw 64 and implant 1 is released again.

FIG. 45 presents a top view of an implant according to FIG. 3 in the shape of a double umbrella that is manufactured from a tube with several slits. The umbrella is formed from a plurality of strips 16 of the same length that are consolidated in a plurality of rhombi. The distal and proximal sides of the umbrella are connected to one another in the peripheral area by diagonal strips 70 that result in the proximal and distal sides of the umbrella being off-set in relation to each other along the length of these diagonal strips 70. This design results in a significant reduction in tension in the peripheral area of the umbrella and, therewith, to reduced danger of breakage.

FIG. 46 presents the slit tube for the embodiment according to FIG. 45 in the first state in which it is not expanded. Tube 2 exhibits a plurality of strips 16 of equal length that are allocated to individual segments of the tube. One of these segments then exhibits strips 70 that run diagonally parallel and that, upon expansion, bring about torsion of the two umbrella halves against each other and, therewith, to a reduction in tension.

FIG. 47 presents another embodiment in the shape of a cut and slit tube 2 respectively with strips 70 that run diagonally parallel in the middle piece 14 of a device 1 in accordance with the invention. The individual strips 70 that run diagonally parallel are connected to one another, section-wise, by bridges 71 in order to achieve a certain stability. The middle piece lies between two umbrellas 5 and 6 of a device in accordance with the invention and aligns itself relatively easily in the case of diagonal strips 70 to the dimensions of a passage to be closed. Self-centring of the implant follows.

FIG. 48 is a top view of a braided umbrella 5 with a plurality of strips 16. The strips in this case are of varying lengths. The individual strips are merged into a circular structure in the centre through terminally located loops and a thread that is guided through these loops which fixes the structure and permits incorporation of the tube 2 in the first state. The surface structure of the individual strips 16 permits great flexibility and prevents breakages that occur due to a high flexural load as well as fatigue breakage.

FIG. 49 presents another variant of the valve-bearing structure of FIG. 23 in which the strips 16 are, in addition, provided with loops 72 at their position near the catheter 12 through which a thread 73 is drawn. The thread 73 is guided through catheter 12 and can be used by the treating doctor to pull the cylindrical structure together and pull the same into the catheter 12 or into a larger catheter surrounding catheter 12. In order to improve in order to improve the pulling-in capacity, proximal strips could be located at different heights so that a staggered pulling-in is possible. This type of design can, for example, be achieved by cutting a diagonally-cut tube with a laser beam.

Valve 78 that is sewed into the umbrella structure is manufactured from a bio-compatible and, considered by itself, established material whereby it must be ensured that this valve can comply with the compression/expansion of the umbrella structure without suffering from any loss in functionality.

FIG. 50 presents a variant of FIG. 49 regarding repositioning. The micro-catheter 12 through which thread 73 is guided, runs within another catheter 74 with radiopaque markers 75 at the distal end. In order to reposition the implant 1, the treating doctor tautens thread 73 resulting in implant 1 being pulled proximally to the diameter of the elongated tube in the first state (FIG. 50*b*). Due to the reversed movement of catheters 12 and 74, implant 1 is then pulled into the other catheter 74 and can, in this manner, be explanted or repositioned (FIG. 50*c*).

It shall be understood that the variants presented in FIGS. 23, 49 and 50 are sectional drawings of spatially designed implants that have been obtained from a cut tube. The illustration of the individual strips have been simplified. It shall also be understood that a corresponding implant 1 can also comprise a braided structure.

It shall be understood that the individual designs and features addressed in the illustrations are examples. Over and above this, the invention comprises every expedient combination of features from the description that fall under the basic conditions of Claim 1.

The invention claimed is:

1. A self-expanding implant for closing of defect openings in human and animal bodies that, in a first state, has the shape of an elongated tube with slit segments and, in a second state, takes on a shorter shape, that defines a proximal and a distal umbrella with a larger lateral extension and a middle piece, the slit segments of the tube forming individual strips (16) that are respectively connected to adjacent strips, the strips forming the proximal and distal umbrellas having equal length so that an overall net-like structure emerges in the second state with an approximately rhombus-shaped or hexagonal-shaped mesh structure, wherein strips of the proximal and distal umbrellas are directly connected to strips of the middle piece, the strips of which in the first state run diagonally parallel in order to reduce tension and for self-centering the implant after implantation, the implant being formed from connected strips of multiple wires that are merged into an annular or tubular shape at both ends, the strips consisting of braided multiple wires and collectively forming approximately quadrangular parallelograms, rhombi or hexagons that are each connected at the tip to the next parallelogram, rhombus or hexagon thereby facilitating retrieval of the implant.

2. Implant according to claim 1 in the form of a netting or fabric.

3. Implant according to claim 1, characterised in that, loops are located at the strips (16) or strips (16) are connected by loops.

4. Implant according to claim 1, characterised in that, in the second state, the implant is designed to deform in radial direction against the wall of the opening to be closed so that it can support itself against the wall and can be positioned approximately centrally within the opening.

5. Implant according to claim 1, characterised in that, the strips exhibited by the middle piece (14) in the first state are connected, section-wise, by bridges, amongst themselves.

6. Implant according to claim 1, characterised in that, it exhibits a coupler at least one end.

7. Implant according to claim 6, characterised in that, the coupler is secured by an inner guidewire (11).

8. Implant according to claim 1, characterised in that, it consists entirely or partially of shape memory materials, particularly nitinol.

9. Implant according to claim 1, characterised in that, it is covered in sub-areas by a membrane.

10. Implant according to claim 1, characterised in that, it is designed in such a manner that it can be repositioned/ explanted.

11. Implant according to claim 10, characterised in that, the hollow structure has loops at its peripheral strips through which a circumferential thread is guided.

12. A self-expanding implant for closing of defect openings in human and animal bodies that, in a first state, has the shape of an elongated tube with slit segments and, in a second state, takes on a shorter shape, that defines a proximal and a distal umbrella with a larger lateral extension and a middle piece, the slit segments of the tube forming individual strips that are respectively connected to adjacent strips, the strips forming the proximal and distal umbrellas having equal length so that an overall net-like structure emerges in the second state with an approximately rhombus-shaped or hexagonal-shaped mesh structure, wherein strips of the proximal and distal umbrellas are directly connected to strips of the middle piece, the strips of which in the first state run diagonally parallel in order to reduce tension and for self-centering the implant after implantation, the implant being formed from connected strips of multiple wires that are merged into an annular or tubular shape at both ends, the strips, the multiple wires collectively forming approximately quadrangular parallelograms, rhombi or hexagons that are each connected at the tip to the next parallelogram, rhombus or hexagon thereby facilitating retrieval of the implant.

* * * * *